United States Patent [19]
Krogh et al.

[11] Patent Number: 5,587,498
[45] Date of Patent: Dec. 24, 1996

[54] METHOD FOR AMIDE PREPARATION

[75] Inventors: James A. Krogh; Anita R. Mokadam, both of Janesville; B. Brian Smith, McFarland, all of Wis.

[73] Assignee: Exxon Chemical Patents, Inc., Baytown, Tex.

[21] Appl. No.: 314,454

[22] Filed: Sep. 28, 1994

Related U.S. Application Data

[63] Continuation of Ser. No. 63, Jan. 4, 1993, abandoned.
[51] Int. Cl.⁶ .................................................. C07C 237/00
[52] U.S. Cl. ......................... 554/69; 564/141; 564/138
[58] Field of Search ............................. 554/69; 564/138, 564/141

[56] References Cited

U.S. PATENT DOCUMENTS

| | | | |
|---|---|---|---|
| 3,056,818 | 10/1962 | Weber et al. | 260/410 |
| 3,801,610 | 4/1974 | Werdhausen et al. | 260/404 |
| 3,816,483 | 6/1974 | Werdehausen et al. | 260/404 |
| 4,032,550 | 6/1977 | White et al. | 260/410 |
| 4,043,941 | 8/1977 | White et al. | 252/430 |
| 4,655,972 | 4/1987 | Eikelboom et al. | 564/138 |
| 4,682,982 | 7/1987 | Steltenkamp et al. | 8/137 |
| 4,804,683 | 2/1989 | Steltenkamp | 514/629 |

*Primary Examiner*—Samuel Barts
*Attorney, Agent, or Firm*—Jansson & Shupe, Ltd

[57] ABSTRACT

A method for amidation of carboxylic acids using a supported transition metal catalyst. The amides prepared by this inventive method are available in high-yield and excellent purity, without catalytic residue.

17 Claims, No Drawings

METHOD FOR AMIDE PREPARATION

RELATED APPLICATION

This application is a continuation of application Ser. No. 08/000,063 filed on Jan. 4, 1993 and now abandoned.

FIELD OF THE INVENTION

This invention is related generally to the synthesis of amides and, more particularly, to methods employing heterogeneous catalysts.

BACKGROUND OF THE INVENTION

As a class of chemical compounds, amides have demonstrated wide utility both as synthetic intermediates and end products in a variety of industrial and commercial applications. Current use includes amides as laundry anti-static agents, detergents, lubricants, foamers, and additives in products as diverse as shampoos and asphalt pavements. Sterically-hindered amides are of particular importance for use as industrial cleaners and insecticides (as described in U.S. Pat. Nos. 4,682,982 and 4,804,683, respectively).

Commercially and on industrial scales, amides are prepared via the condensation reactions of amines with acid chlorides. The later are highly-reactive acylating agents, necessitating stringent reaction control. As with many chlorinated organics, corrosion concerns warrant use of expensive glass-lined reaction vessels. An additional consideration is that the acid chloride is typically prepared by the reaction of either thionyl chloride or phosgene with the corresponding acid. Both reagents present significant toxicity and reactivity concerns which detract from the acid chloride as a useful synthetic intermediate. Moreover, under common preparatory conditions, the amide product is subject to side reactions which tend to decrease yield and introduce unwanted impurities.

An efficient, economical means for large scale amide preparation has been an on-going concern in the art. One approach which has met with some success is homogeneous catalysis, such as that described in U.S. Pat. Nos. 3,816,483 and 3,951,996. Use of a reaction-soluble Group IVb or Vb metal catalyst has alleviated many of the problems which plague more traditional synthetic routes. Generally, good yields in commercial quantities are available directly from the acid without excessive reaction times and/or unfavorable reaction conditions.

However, the prior art has associated with it a number of significant problems and deficiencies. Most are related to undesirable reaction conditions, inadequate yields, and impurities, and result from the catalytic systems currently used.

One major problem of the prior art is that amidation under homogeneous catalytic conditions is rather limited to use of ammonia and then only with a large molar excess relative to the carboxylic reactant. Generally, unacceptable results are obtained when either the acid or amine reactant is mono- or di-substituted at the α-position.

Another significant and well-documented deficiency is that Group IVb and Vb metal compounds tend to hydrolyze with loss of catalytic activity. Inasmuch as water is a by-product of acid amidation, an excessive amount of catalyst may be necessary in order to obtain acceptable yields.

A related problem associated with homogeneous catalysis is residual catalyst, the presence of which tends to haze or discolor the amide product and further contribute to the oxidative, thermal, and/or hydrolytic instability of the amide or any subsequent formulation product.

In summary, a considerable number of drawbacks and problems exist in the art relating to the preparation of amides from carboxylic acids. There is a need for an improved amidation method such that synthetically and commercially useful amides may be prepared efficiently and economically.

OBJECTS OF THE INVENTION

It is an object of this invention to provide an amidation method overcoming the problems of the prior art, including those mentioned above.

It is an object of this invention to provide an amidation method which permits utilization of a wide range of amine and carboxylic acid reactants, including those sterically-hindered, in essentially equimolar quantities.

Another object of this invention is to provide an amidation method whereby the catalytic agent does not lose activity over the course of its reaction cycle, even in the presence of water.

Another object of this invention is to provide an amidation method whereby the reaction product may be isolated quickly and efficiently without contamination by catalytic residue.

These and other important objects will be apparent from the descriptions of this invention which follow.

SUMMARY OF THE INVENTION

This invention is a novel method for the preparation of amides. It overcomes certain well-known problems and deficiencies, including those outlined above.

Batch, continuous, or semi-continuous preparation of amides may be accomplished by reacting an amine with a carboxylic acid at a sufficient temperature in the presence of at least 0.001 weight percent, based on the reactants, of a catalyst containing a transition metal selected from Groups IVb, Vb, and VIb, the transition metal present on and bound to a solid support. The catalyst is obtained by reacting a hydroxylic support with a transition metal compound having structural formula $$M(OR)_n Q_m$$

wherein M is a transition metal selected from Groups IVb, Vb, and VIb; OR is an alkoxy radical; n is an integer from 2 to the valence of metal M; Q is an inert group unreactive with the hydroxyl groups of the support, the alkoxide radical, or alcohol formed therefrom; and m is an integer such that the sum of n and m equals the valence number of metal M.

Preferably, the transition metal component of the catalyst is a transition metal tetralkoxide, with the metal selected from the group consisting of titanium, zirconium, hafnium, and vanadium. Likewise, a preferred hydroxylic support is one selected from the group consisting of silica, alumina, clay, and mixtures thereof.

In preferred embodiments, the catalyst is about 0.05–1.5 weight percent, based on the reactants, with up to about 60 weight percent titanium loading. In highly-preferred embodiments, the catalyst loading is up to about 45 percent titanium.

Likewise, in preferred embodiments, the amine is selected from the group consisting of ammonia, primary amines, and secondary amines. The carboxylic reactant is selected from the group consisting of α-mono- and disubstituted carboxylic acids. In highly-preferred embodiments, the reaction is conducted under elevated pressures, at about 175–600 pounds per square inch, and at temperatures of about 200°–350° C.

As described above, this inventive method may be used to effect amidation directly from the corresponding carboxylic acid, by-passing the hazardous reagents which typify acid halide routes, and without large molar excesses of amine reactant. By reacting essentially equimolar quantities of amine and carboxylic acid, amidation may now be achieved more economically.

As discussed more fully below, this method finds particular utility in the preparation of sterically-hindered amides, a class of chemical compounds found to exhibit insecticidal activity. These compounds may be prepared via methods of the prior art, either from the corresponding acid in low yield, or from the acid halide with somewhat better results, but also with the aforementioned hazards and process deficiencies. Although useful for the preparation of a wide range of amides, the method of this invention provides, in particular, a new and efficient synthetic route to a commercially-important group of chemical compounds.

The catalysts used in conjunction with this method are not deactivated by water. Economic and process benefits are realized by not having to replace or replenish an expensive reagent. This is especially significant under conditions where relatively large amounts of catalyst are necessary, such as with a continuous reaction process.

Because the transition metal is bound to a solid support, it can be essentially removed from the reaction medium. Unlike the homogeneous methods of the prior art, simple filtration techniques may be used effectively. The amidation products may, therefore, be isolated without costly and time-consuming distillation or complexation procedures to remove residual transition metal. Inasmuch as many amides are incorporated into personal care products and must meet stringent quality-control specifications additional cost savings are also realized.

Amenability to routine filtration techniques allow the catalysts to be recovered and/or reused in conjunction with additional reaction sequences. Hydrolytic stability also permits the catalysts to be employed with either continuous or semi-continuous reaction processes—a versatility and advantage not available with catalysts of the prior art.

The transition metal (Groups IVb, Vb, and VIb) component of the inventive catalyst, is preferably titanium, zirconium, hafnium, or vanadium. The metal is incorporated into the catalyst via a transition metal alkoxide having the general structural formula

The alkoxy (OR) radical may contain up to 20 carbon atoms and includes ethoxy, n-propoxy, isopropoxy and like homologs and structural isomers. Higher-molecular weight alkoxides tend to lower amidation yields, presumably by introducing undesirable steric factors and inhibiting catalytic activity. Especially useful transition metal alkoxides include titanium tetraethoxide, titanium tetraisopropoxide, zirconium tetraisopropoxide and hafnium tetraisopropoxide. Titanium tetralkoxides are preferred because of their availability, high degree of reactivity with the hydroxylic support employed, and the superior yields and product purity obtained therewith.

The catalysts of this invention are commercially available. Alternatively, they may be prepared following well-known procedures involving the reaction of a molar excess of transition metal alkoxide with a hydroxylic support. The reaction is typically carried out at an elevated temperature in a hydrocarbon medium and in the presence of water. The supported transition metal so prepared may be used effectively at levels as low as 0.001 weight percent, based on the reactants, or may be utilized in large molar excess where a semi-continuous or a continuous reaction process is employed.

The hydroxylic support upon which the transition metal is bound may be a naturally-occurring material or one commercially manufactured. Typically, the support is a finely-divided particulate, but may also be fibrous in form. While the type of support may vary widely, its surface must contain a plurality of hydroxylic functional groups available to react with and bind the transition metal to the support surface. Materials meeting this requirement include alumina, silica, silica gel, various natural-occurring clays (including kaolinite and smectite types, especially montmorillonite clay) zeolites, aluminates, as well as a variety of others well-known to those skilled in the art. An especially effective catalyst is titanium tetraisopropoxide on powdered clay, available at various transition metal levels from Henkel Chemical Corporation.

The method of this invention is useful with any mono- or polycarboxylic aliphatic, olefinic, aromatic, cyclic or alicyclic acid, including those in which other functionalities are present. Acids which may undergo amidation include acetic, propanoic, n-butyric, isobutyric, phenylacetic, hexanoic, 2-ethylhexanoic, heptanoic, octanoic, caproic, lauric, myristic, palmitic, stearic, oleic, linoleic, linolenic, malonic, succinic, glutaric, adipic, decane-1,10-dicarboxylic, pentadecane-1,15-dicarboxylic, muconic, cyclohexane-1,2,3,4,5,6-hexacarboxylic acid, cyclopentene-2-carboxylic acid, 1-cyclohexene-1-carboxylic acid, and 1,3-cyclohexadiene-1,4-dicarboxylic acid. Suitable aromatic acids include benzoic, the toluic acids, α- and β-naphthoic, phthalic, and various o-, m-, and p- nitro- and alkylsubstituted benzoic acids. High-molecular weight dimer acids (commercially available as a mixture of $C_{34}$ di- and tribasic acids) and polycyclic tertiary rosin acids, as well as derivatives thereof, may also be amidated by this method.

Use of sterically-hindered acids, which are characterized by one or more substituents at the α-carbon may also be used with this method. The supported metal catalyst described herein provides good yields despite steric constraints which impede amidation by prior art methods. The amides of various "neo" acids (α,α-dimethyl aliphatic and olefinic acids, and homologs thereof) are thus readily available, including those from neopentanoic, neoheptanoic, and neodecanoic acids. Of particular synthetic and commercial importance is the reaction of monomethylamine and neodecanoic acid, the product of which demonstrates excellent insecticidal activity, but is otherwise available only in relatively low yield.

The amines which may be used with the method of this invention may be mono- or polyfunctional aliphatic, olefinic, alicyclic, cyclic and aromatic amines, including those in which additional functional substituents—in particular, oxa-substituents which characterize etheramines—are present. By way of illustration, representative amines include ammonia, monomethylamine, the $C_2$–$C_{10}$ monoalkylamines, and the corresponding dialkylamines. Higher molecular weight amines may also be used. Useful polyamines include ethylenediamine, 1,3-propanediamine, 1,4-butanediamine, 3-methyl-1,5-pentanediamine, and the like.

A wide range of reaction conditions may be employed successfully with this method, the exact nature of which are dependent primarily upon the reactants and the type of synthetic procedure utilized. Optimum reaction pressure is observed to be a function of the temperature at which the reaction is conducted and dependent upon whether the resulting amides are prepared by a batch, continuous, or semi-continuous procedure.

Where the reactants have prolonged catalyst contact, as is characteristic of a batch procedure, the temperature required to facilitate the reaction will be relatively low. By contrast, where the catalyst-contact time is relatively short—such as with either a continuous or semi-continuous procedure—it is advantageous to employ higher reaction temperatures and/or pressures. As a general proposition and as described above, the method of this invention is preferably conducted under pressures of about 175–600 psi and about 200°–350° C.

The amine and acid starting materials may either be reacted neat or in the presence of an inert solvent. The primary concern is to optimize process economies and reactant catalyst-contact time, within the parameters of a given procedure, to achieve uniform rate of reaction and maximize yield. In those situations where it is undesirable to use undiluted reactants, acceptable solvents will be apparent to those skilled in the art. Depending upon the reaction process utilized, an especially useful solvent may be one which forms an aqueous azeotrope, such that water may be removed from the reaction medium and move the reaction equilibrium toward completion.

EXAMPLES OF THE INVENTION

Example 1

Illustrating use of this invention with a batch reaction procedure, two moles (360 grams) of neodecanoic acid, a tertiary carboxylic acid obtained from Exxon Chemical Company, and 0.2% (0.72 grams) of a titanium on clay catalyst (Henkel Corp., Emery Group) having a 45% loading of titanium were charged to a two liter stainless steel Parr Inc. high pressure reactor. The reactor was equipped with a 1000 psi pressure gauge, cooling coils, 1500 psi rupture disk, and a vacuum distillation take-off adapter. A vacuum was applied to the system, and then it was sealed.

A five lb. cylinder of anhydrous monomethylamine (MMA) was warmed to 60° C. and a transfer line was connected from the cylinder to the reactor which was placed upon a top loading balance. MMA was then introduced to the reactor until 1.32 moles (41 grams, a 65% theoretical amount based on the acid) were charged. The flow was terminated and heat and agitation were applied. A temperature of 220°–250° C. was maintained for 15 hours with the pressure reaching 300 psi. The contents were then cooled, the pressure vented, and the water of reaction was vacuum stripped. No MMA was detected during the vacuum strip which indicated total conversion to the amide, as verified by the titration of 35% free acid. The MMA addition procedure may be repeated and the reaction continued as described above, with yields in excess of 90%, even where the amine is used in less than stoichiometric amounts.

Example 2

A continuous reaction procedure may also be utilized with the amidation method discussed herein. Accordingly, a continuous column is assembled with a teflon diaphragm pump, then charged with catalyst. A receiver charged with molecular sieves may be installed downstream of the column to act as an absorber for the water liberated during the reaction. A product receiver is situated downstream of the dryer and piped to a pump suction to complete the continuous loop.

The receiver is charged with about equimolar amounts of acid and amine reactants. An exotherm typically occurs during salt formation and the initial pressure gradually falls. The initial pumping temperature is about 150° C. and is raised in 20° increments up to about 250° C. The conversion to amide is noted by a decrease in acid value. Water content of the emerging product may also be monitored by sampling the process stream via sample take-off.

Example 3

Employing the heterogeneous catalytic method of this invention, the following amides are representative of those which may be prepared from the corresponding acids and amines.

| Acid | Amine | Amide |
| --- | --- | --- |
| a) Acetic acid | Ammonia | Acetamide |
| b) Acetic acid | Dimethylamine | N,N-Dimethylacetamide |
| c) 2-Methyl-3-butenoic acid | Methylamine | N,2-Dimethyl-3-butenamide |
| d) 2,2-Dimethylpentanoic acid | Ethylmethylamine | N-Ethyl-N,2,2 trimethyl-pentanamide |
| e) Cyclohexanecarboxylic acid | Ammonia | Cyclohexane-carboxamide |
| f) p-Nitrobenzoic acid | Methylamine | N-Methyl-p-Nitrobenzamide |
| g) Hexane-1,6-dicarboxylic acid | Ammonia | Hexane-1,6-diamide |
| h) Propanoic acid | Piperidine | 1-Propanoylaza-cyclohexane |
| i) Hexadecanoic acid | Dibutylamine | N,N-Dibutylhexa-decanamide |
| j) 2-methylpentanoic acid | Ethenylmethyl-amine | N-Ethenyl-N,2-dimethyl-pentamide |

Example 4

For comparison purposes, the reaction of monomethylamine and neodecanoic acid (1:1 molar ratio, at 440 psi and 250° C. for 18 hours) was also carried out with other catalytic systems.

| Catalyst | % Amide Conversion |
| --- | --- |
| None | 77 |
| Tyzor ®TPT | 75 |
| Zirconium Tetraisopropoxide | 77 |
| K-306 | 79 |
| Titanium tetraisopropoxide on powdered clay | 85 |

This data demonstrates the superior yields possible through use of a supported transition metal catalyst. The results were unexpected in that Tyzor® TPT (available from E.I. dupont de Nemours and Company), used homogeneously, provided a yield lower than that obtained via a non-catalyzed system and lower still when compared to the same reaction conducted in the presence of just the solid clay support. (K-306 is the tradename of a clay available from Sud-Chemie AG, Munich, Germany.)

The reaction was repeated, changing only the amount of catalyst employed. At 0.5, 0.25, and 0.10 weight percent titanium tetraisopropoxide on powdered clay catalyst (from Henkel Corporation), the percent amide conversion remained essentially unchanged.

This example also shows the practical utility of this method in that the reaction product, N,2,2-trimethylheptanamide, is a member of a novel class of compounds exhibiting excellent insecticidal activity.

While the principles of this invention have been described in connection with specific embodiments, it should be understood clearly that these descriptions are made only by way of example and are not intended to limit the scope of the invention. For example, the method of this invention may be employed with a variety of diacids and diamines. Under appropriate reaction conditions, the polyamides so prepared may be used in commercial products or as synthetic intermediates. While this method has been described as particularly useful for amidation of sterically-hindered acids, use of similarly restricted amines are also contemplated. Likewise, it should be understood that the method may also be employed for amidation of acid anhydrides, although under most circumstances preliminary acid conversion to the anhydride would not be advantageous.

What is claimed:

1. A method for the batch, continuous, or semi-continuous preparation of amides from carboxylic acids, comprising reacting an amine with a neo carboxylic acid having five to nineteen carbon atoms and which has an α-carbon that is at least trisubstituted, at a molar ratio of about 1:1, at a sufficient temperature of about 220°–350° C. in the presence of at least 0.001 weight percent, based on the reactants, of a catalyst containing a transition metal selected from Groups IVb, Vb, and VIb, said transition metal present on and bound to a solid support.

2. The method of claim 1 wherein the catalyst is obtained by reacting a hydroxylic support with a transition metal compound having the structural formula

where

M is a transition metal selected from Groups IVb, Vb, and VIb;

OR is an alkoxy radical;

n is an integer from 2 to the valence number of metal M;

Q is an inert group which will not react with the hydroxyl groups of the support, the alkoxide radical, or the alcohol formed therefrom; and m is an integer such that the sum of n and m equal the valence number of metal M.

3. The method of claim 2 wherein the metal compound is a transition metal tetralkoxide.

4. The method of claim 3 wherein the transition metal is selected from the group consisting of titanium, zirconium, hafnium, and vanadium.

5. The method of claim 2 wherein the hydroxylic support is selected from the group consisting of silica, alumina, clay, and mixtures thereof.

6. The method of claim 1 wherein the transition metal is selected from the group consisting of titanium, zirconium, hafnium, and vanadium.

7. The method of claim 6 wherein the transition metal is titanium.

8. The method of claim 1 wherein the support is selected from the group consisting of silica, alumina, clay, and mixtures thereof, said support with up to about 60 weight percent bound transition metal loading.

9. The method of claim 8 wherein the transition metal is titanium.

10. The method of claim 9 wherein the catalyst is about 0.05–1.5 weight percent, based on the reactants, said catalyst loaded with up to about 45 weight percent titanium loading.

11. The method of claim 1 wherein the amine is selected from the group consisting of ammonia, primary amines, and secondary amines.

12. The method of claim 11 wherein the transition metal is selected from the group consisting of titanium, zirconium, hafnium, and vanadium.

13. The method of claim 12 wherein the transition metal is titanium.

14. The method of claim 1 wherein the support is selected from the group consisting of silica, alumina, clay, and mixtures thereof.

15. The method of claim 14 wherein the support is montmorillonite clay.

16. The method of claim 1 wherein the reaction is conducted under elevated pressures.

17. The method of claim 16 wherein the pressure is about 175–600 pounds per square inch.

* * * * *